Feb. 7, 1950 G. W. BENDER, JR Plant Pat. 919
CARNATION PLANT
Filed March 4, 1949
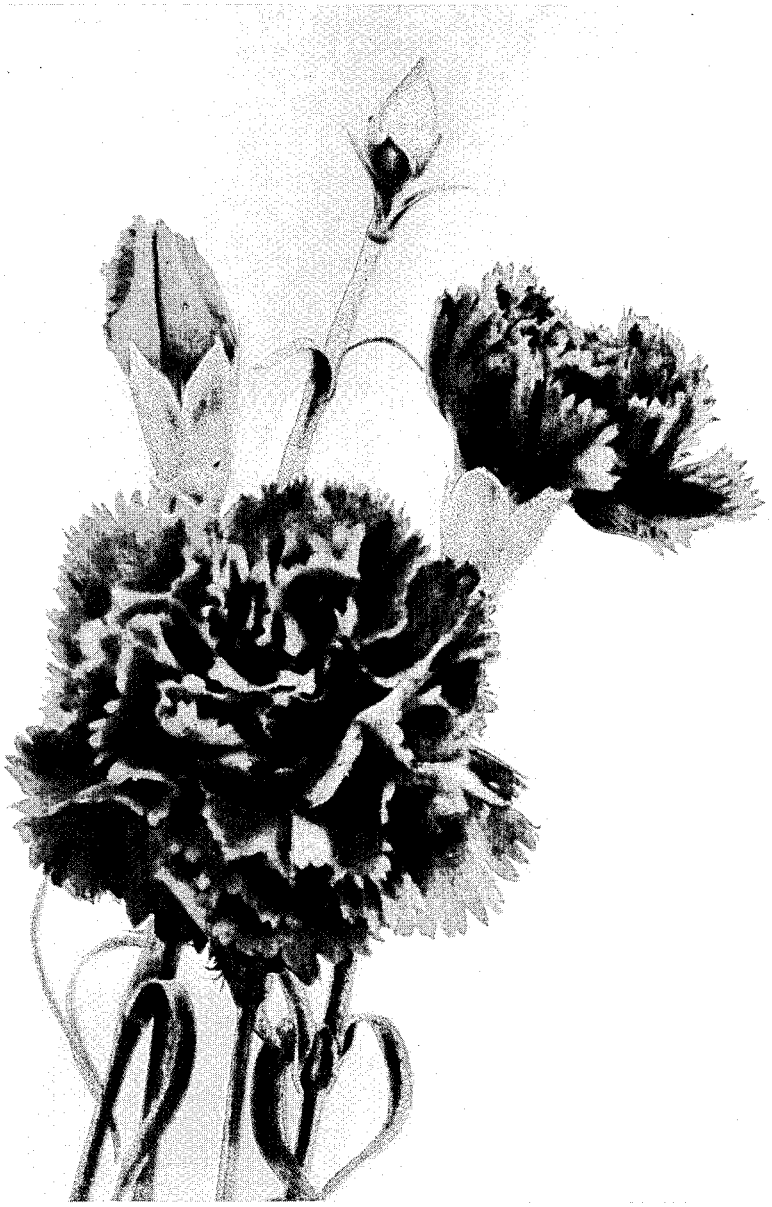
INVENTOR
GEORGE W. BENDER, JR.
BY Robert B Pearson
ATTORNEY Patented Feb. 7, 1950

Plant Pat. 919

UNITED STATES PATENT OFFICE

919

CARNATION PLANT

George W. Bender, Jr., Wyndmoor, Pa.

Application March 4, 1949, Serial No. 79,692

1 Claim. (Cl. 47—60)

My invention relates to a new and distinct variety of carnation plant of the large flowered type commonly known as a greenhouse forcing carnation. It originated from a sport of a smaller carnation known as "Johnson's Crimson."

Carnations according to the present invention possess characteristics similar in some respects to the parent, particularly with regard to stem and foliage. Other characteristics are somewhat similar to the carnation known as the "Mrs. C. W. Weld." Perhaps the most distinctive characteristics of the new carnation reside in the flower itself, particularly with reference to the larger petalage, larger flower with its high and very full center, and its very true crimson color which lacks any white streaks.

In accordance with the invention the new carnation plant is vigorous and consistent in growth. It is erect and clean. Not only is it disease resistant, but experience has shown that it is tolerant of the usual insecticides, fungicides and gases employed in carnation growing. The plant may be grown in a greenhouse or in the fields.

Reference is made to the accompanying color representation of my new carnation plant which will now be described in detail. The color terminology employed conforms to Ridgeway's Color Standard where plate numbers are given. Otherwise the ordinary dictionary definitions shall obtain.

Type: Tall; erect, hardy; greenhouse; sport; for cut flowers.

Breeding or discovery: Sport. *Parent*—"Johnson's Carnation."

Propagations: The distinguishing characteristics are maintained through successive propagations by cuttings.

Locality where grown: In greenhouses and in fields, in Philadelphia, Pennsylvania.

Type of soil in which grown: Any soil in which other carnations are grown, which, preferably, is a light soil which is slightly on the alkaline side and rich in potash.

*The plant*

Foliage:

*Leaves.*—Moderate in quantity; seldom curled; medium to narrow in width. (Narrower than leaves on the "Mrs. C. W. Weld.") *Color*—ranges from "Pistachio Green" to "Dark American Green." Plate XLI, with a heavy grey bloom on foliage.

Foliage—Continued

*Stems.*—Erect; clean; stronger than usual; wiry; long. Internodes, average. *Color*—same color as leaves except for a light reddish coloring at nodes. The foliage is of a lighter nature than the "Mrs. C. W. Weld."

Growth:

*Characteristics.*—Vigorous; strong; medium in height—32 to 38 inches. Medium bush without grassiness.

*Habit.*—Vigorous. Produces well and very consistent in producing good quality blooms. *Place of growth*—Grown on the private estate of Mr. V. A. Lea, E. Gravers Lane and Flourtown Ave., Chestnut Hill, Philadelphia 18, Pa.

*The flower*

Bud:

*Color.*—Same as bloom, as hereinafter described.

*Shape.*—Pear-shaped just before color shows.

*Size.*—Large, 1⅛'' to 1¼'' long.

*Calyx.*—Very broad and blunt. Exceedingly strong and tough. Slightly over 1½'' in length and 1 inch wide. Very seldom splits.

Bloom:

*Color.*—Crimson-red in the generally accepted paint nomenclature. The nearest color in Ridgeway's Color Standard is Plate I, "Carmine" to "Oxblood Red" in the depths. Pure even tone, uniformly spread over the visible portion of the petal and extends down over half way on the shank. Does not fade or show black tips as do many crimsons.

*Form.*—High centered, very full. Irregular petals, crinkled and tightly bunched. Crown of bloom is high compact, has no open center.

*Petalage.*—Many. From 56 to 66 petals including petaloids. Petals longer than the "Mrs. C. W. Weld."

*Petals.*—Very many and feathery. Ovate in shape, with long shank. Lacinated or deeply fringed on edge. Outside petals measure from 1¾'' to 2'' across and over 2½'' in length. Silken texture.

*Fragrance.*—Light cinnamon fragrance.

*Shape.*—Circular and fringed with a rounded top.

*The reproductive organs*

Stamens: 10 to 12. Long and slender. White tinged with pink.
Ovary: Medium to small in size.
Pistils: One in number. About one inch long. Never visible in open flower. Color ranges from crimson-red to pink.
Filaments: About one inch long. Color, white tinged with crimson-red.
Anthers: Small. Color, crimson-red. One for each stamen.
Styles: Three, white, topped with approximately "Carmine." Arched and tapering, light.
Pollen: Very sparse. Color—lilac-grey.
Stigma: Small and white, pinhead shaped.
Sepals: Strong, bright green with grey bloom, neat in shape. Five in number. Permanent.
Seeds: Numerous and small.

*Characteristics with regard to disease*

This carnation is resistant to carnation diseases. It also does not appear to be affected by the usual insecticides, fungicides, and gases ordinarily used in carnation growing.

I claim:

A new and distinct variety of carnation plant, characterized as to novelty primarily by its non-fading crimson-red color of pure even tone, uniformly spread over the visible portion of the petal and extending over half way on the shank, and free from black tips, combined with the habit of vigorous growth, productivity, and disease resistance, substantially as shown and described.

GEORGE W. BENDER, Jr.

No references cited.